(12) United States Patent
Hoshino et al.

(10) Patent No.: US 6,361,978 B1
(45) Date of Patent: *Mar. 26, 2002

(54) PRODUCTION OF BIOTIN

(75) Inventors: Tatsuo Hoshino, Kamakura; Akira Asakura, Fujisawa; Tatsuya Kiyasu, Fujisawa; Yoshie Nagahashi, Fujisawa, all of (JP)

(73) Assignee: Roche Vitamins, Inc., Parsipanny, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/840,059

(22) Filed: Apr. 24, 1997

(30) Foreign Application Priority Data

Jun. 5, 1996 (EP) .............................. 96107064

(51) Int. Cl.$^7$ ................................ C12P 17/18
(52) U.S. Cl. .................. 435/119; 435/117; 435/252.33
(58) Field of Search ................ 435/117, 119, 435/252.1, 252.33, 252.3

(56) References Cited

FOREIGN PATENT DOCUMENTS

| EP | 747 483 | 12/1996 |
|---|---|---|
| JP | 61-149091 | 7/1986 |
| JP | 62-155081 | 7/1987 |
| JP | 2-27980 | 1/1990 |
| JP | 3-180174 | 8/1991 |
| JP | 3-240489 | 10/1991 |
| JP | 7-236493 | 9/1995 |
| WO | 87/01391 | 3/1987 |
| WO | 94/08023 | 4/1994 |

OTHER PUBLICATIONS

Flint, D., *J. Biol. Chem.* (1996), 271(27), 16068–16074.*
Beynon, J., et al., *Journal of Bacteriology*, 169(9):4024–4029 (1987).
Birch, O., et al., *The Journal of Biological Chemistry*, 270(32):19158–19165 (1995).
Cleary, P., et al., *Journal of Bacteriology*, 112 (2):830–839 (1972).
Dean, D., et al., *Journal of Bacteriology*, 175:6737–6744 (1993).
Eisenberg, M., et al., *Antimicrobial Agents & Chemotherapy*, 21:5–10 (1982).
Ifuku, O., et al., *Biosci. Biotech. Biochem.*, 56(11):1780–1785 (1992).
Ikufu, O., et al., *Eur. J. Biochem.*, 224:173–178 (1994).
*Industrial Property*, 1:26–34 (1991).
Mayerl, F., et al., *Journal of Bacteriology*, 172:6061–6065 (1990).
Méjean, A., et al., *Biochem. & Biophysical Res. Commun.*, 217(3):1231–1237 (1995).
Mulliez, E., et al., *J. Biol. Chem.*, 268:2296–2299 (1993).
*Nature*, 237 :102–103 (1972), Dixon, et al.
Otsuka, A., et al., *The Journal of Biological Chemistry*, 263(36):19577–19585 (1988).
Sanyal, I., et al., *Archives of Biochemsitry and Biophysics*, 326(1):48–56 (1996).
Sanyal, I., et al., *Biochemistry*, 33:3625–3631 (1994).
Zheng & Dean, *J. Biol. Chem.*, 269(29):18723–18726 (1994).
Zheng, et al., *PNAS*, 90:2754–2758 (1993).
Ohshiro, et al., *Biosci. Biotech. Biochem.*, 59(5):943–944 (1995).
Fu, et al., *Biochemistry*, 33:13455–13463 (1994).
Partial English translation of JP 06 339 371 (1994).
Collins, C. M. et al., "Identification of a nitrogen–regulated promoter controlling expression of *Klebsiella pneumoniae* urease genes," Molecular Biology 8(1) 187–198 (1993).
Roberts, G.P. et al., "Genetics and regulation of nitrogen fixation," Ann. Rev. Microbiol. 35:207–35 (1981).
Hill, S. et al., "Nitrogen fixation gene (nifL) involved in oxygen regulation of nitrogenase synthesis in *K. pneumoniae*," Nature 290:424–426 (1981).

* cited by examiner

*Primary Examiner*—Irene Marx
(74) *Attorney, Agent, or Firm*—Bryan Cave LLP

(57) ABSTRACT

The present invention provides processes for making biotin from desthiobiotin by either contacting desthiobiotin with an enzyme reaction mixture containing bioB gene product and nifU gene product and/or nifS gene product and isolating the biotin or cultivating a microorganism transformed with DNA encoding the bioB gene product, nifU gene product and nifS gene product and isolating the biotin.

13 Claims, No Drawings

PRODUCTION OF BIOTIN

This invention relates to a fermentative process for the production of biotin from desthiobiotin.

BACKGROUND OF THE INVENTION

Biotin is one of the essential vitamins for nutrition of animals, both human and non-human, plants, and microorganisms, and very important as a medicine or food additive.

There are many studies on fermentative production of biotin. Escherichia strains are known as microorganisms which can be used for the above process [see Japanese Patent Publication (Kokai) No. 149091/1986, WO 87/01391 and Japanese Patent Publication (Kokai) No. 155081/1987]. In addition to the above-mentioned strains, Bacillus strains [Japanese Patent Publication (Kokai) No. 180174/1991), Serratia strains [Japanese Patent Publication (Kokai) No. 27980/1990] and Brevibacterium strains [Japanese Patent Publication (Kokai) No. 240489/1991] are also known. But these processes have not yet been suitable for industrial use because of the low efficiency of carbon recovery from the nutrients into biotin and, in some cases, the accumulation of the direct intermediate, desthiobiotin. It is therefore desirable to improve the efficiency of the conversion of desthiobiotin to biotin. A conversion reaction of desthiobiotin to biotin using the resting cell system of *Escherichia coli* (Antimicrob. Agents Chemother. 21, 5, 1982) and one using cell-free extract of *Escherichia coli* [J. Biol. Chem., 270, 19158 (1995); Biosci. Biotechnol. Biochem., 56, 1780 (1992); Eur. J. Biochem., 224, 173 (1994); Arch. Biochem. Biophys., 326, 48 (1996)] are known. According to these publications, it has been clarified that protein factors such as ferredoxin-NADP reductase and flavodoxin together with biotin synthase are involved in the biotin formation from desthiobiotin. Nevertheless, only limited effect has been observed for biotin production from desthiobiotin under these conditions. It was simply speculated that another unknown protein should be involved in this reaction to more efficiently convert desthiobiotin to biotin.

Furthermore. a conversion reaction by using the purified biotin synthase of *Bacillus sphaietricus* with photoreduced deazaflavin as an artificial electron donor instead of using physiological electron transfer system of ferredoxin-NADP reductase and flavodoxin has recently been reported [Biochem. Biophys. *Res. Commun.*, 217, 1231 (1995)]. But the reported reaction efficiency is not high enough for the reaction to be usable in the industrial production of biotin.

An object of the present invention is to find a more efficient process of producing biotin from desthiobiotin, and to this end there have been elucidated various protein factors. It has been found that nifU and nifS gene products (hereinafter referred to as NIFU and NIFS), which are suggested to be involved in the mobilization of the iron and sulfide necessary for nitrogenase metallocluster core formation [J. Bacteriology, 175, 6737 (1993)], are significantly effective for the production of higher amount of biotin from desthiobiotin. The present invention is based upon these findings.

Accordingly, the present invention provides a process for the production of biotin from desthiobiotin which comprises contacting desthiobiotin with an enzyme reaction system containing bioB gene product (which encodes biotin synthase; hereafter referred to as BIOB) and also NIFU and/or NIFS, and isolating the resulting biotin from the reaction mixture, especially such a process wherein BIOB is derived from *Escherichia coli* and NIFU and/or NIFS are derived from *Klebsiella pneumoniae*, or a process as described before wherein the enzyme reaction mixture further contains S-adenosylmethionine, L-cysteine and an electron supplying system, e.g. wherein the electron supplying system comprises NADPH, ferredoxin-NADP reductase and flavodoxin or wherein the electron supplying system comprises deazariboflavin or a functional equivalent component thereof selected from deazaflavin (5-deazaflavin) [J. Biol. Chem., 268, 2296 (1993)] and 8-hydroxy-5-deazaflavin [J. Bacteriology, 172, 6061 (1990)].

It is furthermore an object of the present invention to provide a process as described above wherein the reaction is effected at a pH of from about 6.0 to about 8.5, preferably from about 7.0 to about 8.0, and in a temperature range of from about 20 to about 45 C, preferably from about 25 to about 40 C.

Furthermore, the present invention also provides a fermentative process for the production of biotin from desthiobiotin which comprises cultivating a microorganism, which has been transformed by the DNA sequences encoding BIOB and NIFU and/or NIFS itself or comprised by a single or independent from each other by several plasmids in the presence of desthiobiotin and in an aqueous nutrient medium, and isolating the resulting biotin from the culture medium, especially such a process wherein the microorganism is selected from the genus Escherichia and specifically a process wherein the cultivation is effected for from about 1 to about 5 days, preferably from about 1 to about 3 days, at a pH of from about 5 to about 9, preferably from about 6 to about 8, and in a temperature range of from about 10 to about 45 C, preferably from about 25 to about 40 C.

SUMMARY OF THE INVENTION

The present invention provides a process for making biotin which comprises contacting desthiobiotin with an enzyme reaction mixture comprising a bioB gene product and an additional gene product selected from nifU gene product, nifS gene product, and a combination thereof to form biotin and then isolating the biotin from the reaction mixture. One preferred reaction mixture contains the bioB gene product and the nifU gene product and another preferred reaction mixture contains the bioB gene product and the nifS gene product. The most preferred reaction mixture contains the bioB gene product, the nifU gene product, and the nifS gene product. The reaction mixture can further contain S-adenosylmethionine, L-cysteine, and an electron supplying system selected from NADPH, ferredoxin-NADP reductase, flavodoxin and deazariboflavin or its functional equivalent component selected from deazaflavin and 8-hydroxy-5-deazaflavin.

It is preferred that the reaction mixture contains the bioB gene product, the nifU gene product, and the nifS gene product. The bioB gene product preferably is from *Escherichia coli* and the nifU and nifS gene products are preferably from *Klebsiella pneumoniae*.

Preferably, the process occurs at a temperature of from about 25° C. to about 45° C., more preferably from about 25° C. to about 40° C., and a pH of from about 6.0 to about 8.5, more preferably from about 7.0 to about 8.0.

The present invention also provides a process for making biotin by fermentation comprising the steps of cultivating, in an aqueous nutrient medium, a microorganism transformed with a plasmid containing the DNA encoding bioB gene product and additional DNA selected from DNA encoding nifU gene product, DNA encoding nifS gene product and both the DNA encoding nifu gene product and the DNA encoding nifS gene product with desthiobiotin, producing and accumulating biotin in the aqueous medium, and isolating the biotin from the aqueous medium. The plasmid containing the DNA encoding bioB gene product preferably additionally contains the DNA encoding nifU gene product and the DNA encoding nifS gene product.

Preferably, the cultivation occurs at a time of from about 1 to about 5 days, preferably from about 1 to about 3 days, at a pH of from about 5 to about 9, preferably from about 6 to about 8, and at a temperature of from about 10° C. to about 45° C., preferably from about 25° C. to about 40° C.

Additionally, the present invention provides a process for making biotin by fermentation comprising the steps of cultivating, in an aqueous nutrient medium, a microorganism transformed with a plasmid containing the DNA encoding bioB gene product, the DNA encoding nifU gene product, and the DNA encoding nifS gene product with destiobiotin, producing and accumulating biotin in the aqueous medium, and isolating the biotin from the aqueous medium.

Preferably, the cultivation occurs at a time of from about 1 to about 5 days, preferably from about 1 to about 3 days, at a pH of from about 5 to about 9, preferably from about 6 to about 8, and at a temperature of from about 10° C. to about 45° C., preferably from about 25° C. to about 40° C.

The present invention also provides for a process for making biotin by fermentation comprising the steps of cultivating, in an aqueous nutrient medium, a microorganism transformed with a plasmid containing DNA encoding bioB gene product and an additional plasmid(s) selected from a plasmid containing DNA encoding nifU gene product, a plasmid containing DNA encoding nifS gene product, a combination of both the plasmid containing DNA encoding nifU gene product and the plasmid containing DNA encoding nifS gene product, or a hybrid plasmid containing both the DNA encoding nifU gene product and the DNA encoding nifs gene product, with desthiobiotin, producing and accumulating biotin in the aqueous medium, and isolating the biotin from the aqueous medium.

Preferably, the cultivation occurs at a time of from about 1 to about 5 days, preferably from about 1 to about 3 days, at a pH of from about 5 to about 9, preferably from about 6 to about 8, and at a temperature of from about 10° C. to about 45° C., preferably from about 25° C. to about 40° C.

The present invention also provides for a process for making biotin by fermentation comprising the steps of cultivating, in an aqueous nutrient medium, a microorganism transformed with a plasmid containing DNA encoding bioB gene product, a plasmid containing, DNA encoding nifU gene product and a plasmid containing DNA encoding nifS gene product, with desthiobiotin, producing and accumulating biotin in the aqueous medium, and isolating the biotin from the aqueous medium. Preferably, the cultivation occurs at a time of from about 1 to about 5 days, preferably from about 1 to about 3 days, at a pH of from about 5 to about 9, preferably from about 6 to about 8, and at a temperature of from about 10° C. to about 45° C., preferably from about 25° C. to about 40° C.

DETAILED DESCRIPTION OF THE INVENTION

The present invention provides a process for making biotin which comprises contacting desthiobiotin with an enzyme reaction mixture comprising a bioB gene product and an additional gene product selected from nifU gene product, nifS gene product, and a combination thereto to form biotin and then isolating the biotin from the reaction mixture. One preferred reaction mixture contains the bioB gene product and the nifU gene product and another preferred reaction mixture contains the bioB gene product and the nifS gene product. The most preferred reaction mixture contains the bioB gene product, the nifU gene product, and the nifS gene product. The reaction mixture can further contain S-adenosylmethionine, L-cysteine, and an electron supplying system selected from NADPH, ferredoxin-NADP reductase, flavodoxin and deazariboflavin or its functional equivalent component selected from deazaflavin (5-deazaflavin) and 8-hydroxy-5-deazatlavin.

It is preferred that the reaction mixture contains the bioB gene product, the nifU gene product, and the nifS gene product. The bioB gene product preferably is from *Escherichia coli* and the nifU and nifS gene products are preferably from *Klebsiella pneumoniae*.

Preferably, the process occurs at a temperature of from about 25° C. to about 45° C., more preferably from about 25° C. to about 40° C., and a pH of from about 6.0 to about 8.5, more preferably from about 7.0 to about 8.0.

The present invention also provides a process for making biotin by fermentation comprising the steps of cultivating, in an aqueous nutrient medium, a microorganism transformed with a plasmid containing the DNA encoding bioB gene product and additional DNA selected from DNA encoding nifU gene product. DNA encoding nifS gene product and both the DNA encoding nifU gene product and the DNA encoding nifS gene product with desthiobiotin, producing and accumulating biotin in the aqueous medium, and isolating the biotin from the aqueous medium. The plasmid containing the DNA encoding bioB gene product preferably additionally contains the DNA encoding nifU gene product and the DNA encoding nifS gene product.

Preferably, the cultivation occurs at a time of from about 1 to about 5 days, preferably from about 1 to about 3 days, at a pH of from about 5 to about 9, preferably from about 6 to about 8, and at a temperature of from about 10° C. to about 45° C., preferably from about 25° C. to about 40° C.

Additionally, the present invention provides a process for making biotin by fermentation comprising the steps of cultivating, in an aqueous nutrient medium, a microorganism transformed with a plasmid containing the DNA encoding bioB gene product, the DNA encoding nifU gene product, and the DNA encoding nifS gene product with desthiobiotin, producing and accumulating biotin in the aqueous medium, and isolating the biotin from the aqueous medium.

Preferably, the cultivation occurs at a time of from about 1 to about 5 days, preferably from about 1 to about 3 days, at a pH of from about 5 to about 9, preferably from about 6 to about 8, and at a temperature of from about 10° C. to about 45° C., preferably from about 25° C. to about 40° C.

The present invention also provides for a process for making biotin by fermentation comprising the steps of cultivating, in an aqueous nutrient medium, a microorganism transformed with a plasmid containing DNA encoding bioB gene product, a plasmid containing DNA encoding nifU gene product and a plasmid containing DNA encoding nifS gene product, with desthiobiotin, producing and accumulating biotin in the aqueous medium, and isolating the biotin from the aqueous medium. Preferably, the cultivation occurs at a time of from about 1 to about 5 days, preferably from about 1 to about 3 days, at a pH of from about 5 to about 9, preferably from about 6 to about 8, and at a temperature of from about 10° C. to about 45° C., preferably from about 25° C. to about 40° C.

The enzyme reaction system or mixture used in this invention contains BIOB, NIFU and/or NIFS as protein factors. As the BIOB for the above reaction, a cell-free extract of the cells containing BIOB or the BIOB partially or completely purified through conventional isolation methods for enzymes can be used. Any kind of BIOB which has biotin synthase activity can also be used for this reaction, but it is preferable to use *Escherichia coli* BIOB. If desired, a large amount of purified BIOB can be obtained by the following procedures. A gene library of *Escherichia coli* containing an appropriate length of DNA fragment covering the full size of the coding region of the bioB gene is constructed. Because it has been known that the *Escherichia coli* bioB gene is located in a 1.3 Kb NcoI-HaeIII fragment [J. Biol. Chem., 263, 19577 (1988)], these two restriction enzymes can conveniently be used. A variety of vector plasmids to be used for this purpose is available from commercial suppliers. The vector plasmid pTrc99A, obtainable from Pharmacia Biotech Co., is one of the inducible plasmids generally used in the art. Then, mixed hybrid plasmid DNAs from the gene library are extracted from the mixed culture of the above *Escherichia coli* strains, and are used to transform bioB gene-deficient mutant of *Escherichia coli*. *Escherichia coli* R875 [bioB 17; J. Bacteriol., 112, 830 (1972)] is suitable for this purpose. The clones showing biotin prototrophy are selected based on the expression of the objective bioB gene. This clone should contain the bioB gene and express it. Any hybrid plasmid showing this property can be used to obtain BIOB. The hybrid plasmid named pTrcEB1 is one of the objective plasmids. To obtain a large amount of BIOB, *Escherichia coli* JM109 (Takara Shuzo Co., Shiga, Japan) transformed by pTrcEB1 by a suitable cell method is cultivated in a nutrient medium with induction, and the produced BIOB can be isolated by using the general chromatography technologies. As an alternative, the *Escherichia coli* bioB gene expression plasmid can be constructed according to the known procedures disclosed in Japanese Patent Publication (Kokai) No. 149091/1986 or Japanese Patent Publication (Kokai) No. 236493/1995.

As the NIFU and NIFS for the above reaction. a cell-free extract of the cells containing the above proteins of the NIFU and NIFS, or NIFU and NIFS partially purified through conventional isolation methods for enzymes, can be used. Any kind of NIFU and NIFS having the effects on biotin formation from desthiobiotin can be used for this reaction. But it is preferable to use *Klebsiella pneumoniae* NIFU and NIFS. *Klebsiella pneumoniae* M5a1 is a well characterized strain having the nifU and nifS genes. The nifU and nifS genes of *Klebsiella pneumoniae* are obtained by the following procedures. A gene library of *Klebsiella pneumoniae* M5a1 is first constructed by using DNA fragment cut by a restriction enzyme such as BamH1. Because it has been known that a 2.5 Kb BamH1 fragment of the *Klebsiella pneumoniae* chromosomal DNA contains the objective nifU and nifS genes [J. Bacteriol., 169, 4024 (1987)], DNA fragments of 2.3–2.6 Kb in length are collected and ligated with any vector plasmids which are replicable in appropriate microorganisms. The vector plasmid pUC19 (Takara Shuzo Co.) with *Escherichia coli* JM109 is one of the suitable combinations of a plasmid and host microorganism to construct a gene library. Then the objective clones can be selected by conventional methods such as colony hybridization using synthesized oligonucleotide probes prepared based on the published DNA sequence of nifU and nifS genes.

Subsequently, the DNA fragment harboring the nifU and nifS genes can be subcloned into other expression vector plasmids. The inducible vector plasmid such as pTrc99A can favorably be used to express the nifU and nifS genes. *Escherichia coli* JM109 (pKNnif04) is one of the suitable clones to express nifU and nifS genes. Based upon the published DNA sequences of bioB, nifS and nifU which can be obtained from any known sequence databank, e.g. the European Bioinformatics Institute (Hinston Hall, Cambridge, GB) DNA sequences encoding such genes can also be synthetically constructed by methods known in the art, e.g. see EP 747 483. DNA sequences encoding any BIOB, NIFU or NIFS can be isolated from any microorganisms based on published sequences using the well known PCR Technology. Such microorganisms can be obtained from any known depository authority listed in the journal "Industrial Property" [(1991) 1, 29–40], e.g. the American Type Culture Collection (ATCC).

Cultivation of the microorganisms used in the present invention can be effected by using known procedures. An aqueous medium containing an assimilable carbon source, a digestible nitrogen source, an inorganic salt, and other nutrients necessary for the growth of the microorganism can be used as the aqueous nutrient (culture) medium. As the carbon source, for example, glucose, fructose, lactose, galactose, sucrose, maltose, starch, dextrin or glycerol may be employed. As the nitrogen source, for example, peptone, soybean powder, corn steep liquor, meat extract, ammonium sulfate, ammonium nitrate, urea or a mixture any of these may be employed. Furthermore, as the inorganic salt, a sulfate, hydrochloride or phosphate of calcium, magnesium, zinc, manganese, cobalt or iron may be employed. And, if necessary, conventional nutrient factors or an antifoaming agent, such as animal oil, vegetable oil or mineral oil can also be included in the aqueous nutrient medium. If the obtained microorganism has antibiotic resistant marker, relevant antibiotic can also be included in the medium. If the expression of the objective genes are inducible by isopropyl-beta-D-thiogalactopyranoside (IPTG), this compound can also be present in the medium. The pH of the culture medium is suitably from about 5 to about 9, preferably from about 6 to about 8. The cultivation temperature range is suitably from about 10 to about 45° C., preferably from about 25° C. to about 40° C. The cultivation time is normally from about 1 to about 5 days, preferably from about 1 to about 3 days.

For the preparation of cell-free extract from the obtained cells by cultivation, general methods such as sonication, cell breakage in the presence of glass beads or by French press can be applied. After cell breakage, the obtained solution is centrifuged to separate the cell debris, and its supernatant can be used as a cell-free extract.

The enzyme reaction system contains as the reactive components BIOB and also NIFU and/or NIFS proteins in the cell-free extracts as prepared above or those partially purified. In addition to the above proteins, desthiobiotin is added as the substrate for this reaction. The amount of desthiobiotin to be added can be varied depending on the enzyme reaction system employed. Both D-form and a mixture of D- and L-form desthiobiotin can be used as the substrate. The addition of S-adenosylmethionine, L-cysteine and an electron supplying system, such as deazariboflavin or a functional equivalent component of deazariboflavin, stimulates the reaction. Instead of the electron supplying system deazariboflavin or its functional equivalent component selected from deazaflavin (5-deazaflavin) and 8-hydroxy-5-deazaflavin (more particularly as an artificial electron donor) for the reaction, ferredoxin-NADP reductase and flavodoxin together with NADPH can be employed as a physiological electron supplying system for the reaction. The optimum concentrations of these additive components can vary depending on the employed enzyme reaction system. But in general, from about 50 μM to about 2 mM for S-adenosylmethionine, from about 10 μM to about 2 mM for L-cysteine and from about 10 to about 1000 μM for deazariboflavin are recommended.

For proceeding the reaction, buffer solution which has no negative influence on biotin formation can be used. Tris-HCl buffer is preferably used. The enzyme reaction is suitably effected at a pH in the range of from about 6.0 to about 8.5, more preferably in the range of from about 7.0 to about 8.0. The reaction temperature is suitably between about 20° C. and about 45° C., more preferably between about 25° C. and about 40° C. If deazariboflavin or its functional equivalent component selected from deazaflavin (5-deazaflavin) and 8-hydroxy-5-deazaflavin is used for stimulating the reaction, this is suitably started or initiated by photoreduction using a fluorescent lamp located about 10 cm away from the reaction mixture. The incubation period may be between 30 minutes and 3 hours. Much longer incubation can be effected so long as the enzymes are active.

Besides the enzyme reaction system as described above, it is also useful to directly use nifU and nifS genes. For example, the bioB, nifU and nifS genes prepared as described before may be placed on one plasmid or on multiple independent plasmids, and introduced into host microorganism such as *Escherichia coli* by a conventional transformation method. Then the biotin production from desthiobiotin can be carried out under a growing system, a resting system and, if desired, an enzyme reaction system using the cell-free extract of the above mentioned microorganism. Any *Escherichia coli* strains modified to overexpress bioB, nifU and nifS genes together can favorably be used. Among these strains, particularly preferred strains are *Escherichia coli* JM109 (pTrcEB1, pKNnif05) and *Escherichia coli* JM109 (pKNnif06).

The biotin produced from desthiobiotin under the conditions as described above can easily be recovered. For this purpose a process generally used for extracting a certain product from its solution may be employed which is applicable to the various properties of biotin. Thus, for example, after solid materials have been removed from the solution, the biotin in the filtrate is absorbed on active carbon, then eluted and purified further with an ion exchange resin. Alternatively, the filtrate is applied directly to an ion exchange resin and, after the elution, the desired product is recrystallized from a mixture of alcohol and water.

The following biological material was deposited under the terms of the Budapest Treaty with the DSMZ-Deutsche Sanmmlung Von Mikroorganismen und Zellkulturen GmbH (DSMZ), at Mascheroder Weg 1b, D-38124 Braunschweig, Germany, and the bacterial strains were assigned the following accession nunbers:

| Strain | Accession No. | Date of Deposit |
|---|---|---|
| *Escherichia coli* JM109 (pTrcEB1) | DSM 14248 | April 23, 2001 |
| *Escherichia coli* JM109 (pKNnif04) | DSM 14249 | April 23, 2001 |
| *Escherichia coli* JM109 (pKNnif06) | DSM 14250 | April 23, 2001 |
| *Escherichia coli* JM109 (pTrcEB1, pKNnif05) | DSM 14251 | April 23, 2001 |

The present invention will be explained in more detail by referring to the following Examples; however, it should be understood that the present invention is not limited to those particular Examples.

EXAMPLE 1

Cloning and Expression of *Escherichia coli* bioB gene (1) Preparation of the whole DNA

*Escherichia coli* HB101 [J. Mol. Biol., 41, 459 (1969); Takara Shuzo Co.] was cultured in 100 ml of Luria broth (LB) medium (1% tryptone, 0.5% yeast extract 0.5% NaCl; pH7.5) at 37° C. for 10 hours, and bacterial cells were recovered by centrifugation. The whole DNA was extracted from cells by the phenol method (Experiments with gene fusions, Cold Spring Harbor Laboratory Press 1984. pp. 137–139; Sambrook et al. 1989 "Molecular Cloning", Cold Spring Harbor Laboratory Press), and 0.7 mg of the whole DNA was obtained.

(2) Preparation of the Genomic library

3 μg of the whole DNA was completely digested with NcoI and HaeIII, and the DNA fragments of 1.2–1.5 kb were isolated by the agarose gel electrophoresis. The DNA fragments were ligated with the vector plasmid pTrc99A (Pharmacia Biotech Co., Pharmacia, Uppsala, Sweden) digested with NcoI and SmaI using the DNA ligation Kit (Takara Shuzo Co., Japan) according to the instructions of the manufacturer. The ligation mixture was transferred into *Escherichia coli* strain JM109 [Gene, 33, 103 (1985)] by a suitable cell method (Molecular Cloning, Cold Spring Harbor Laboratory Press 1982, pp. 252–253), and the strains were selected for ampicillin resistance (100 μg/ml) on LB medium agar plate. 3,000 of individual clones having the genomic DNA fragments inserted at the downstream of the strong hybrid trypophane/lactose promoter [Gene 69, 301–315 (1988); hereinafter "trc promoter"] were obtained as a genomic library.

The ampicillin resistant strains having the genomic library were cultured at 37° C. for 16 hours in 50 ml of LB medium containing 100 μg/ml ampicillin. and bacterial cells were collected by centrifugation. Plasmid DNA pool was extracted from the bacterial cells by the alkaline-denaturation method (Molecular Cloning, Cold Spring Harbor Laboratory Press 1982, pp. 90–91).

(3) Selection of the hybrid plasmid having *Escherichia coli* bioB gene

The plasmid DNA pool was transferred into *Escherichia coli* bioB deficient mutant R875 [J. Bacteriol. 112, 830–839 (1972)] by a suitable cell method. To obtain a clone carrying the bioB gene, the transformants were selected for resistance to ampicillin and for biotin prototrophy on LB medium agar plate containing 100 μg/ml ampicillin, 0.075 U/ml avidin and 0.1 mM isopropyl-beta-D-thio-galactopyranoside (IPTG).

One of the obtained transformants was cultivated in LB medium containing 100 μg/ml ampicillin, and the hybrid plasmid was extracted from the cells. The isolated plasmid was ahalyzed using restriction enzymes. The hybrid plasmid had a 1.3 kb of NcoI-HaeIII fragment containing the bioB gene and was designated pTrcEB1. *Escherichia coli* strain JM109 having this plasmid was named *Escherichia coli* JM109 (pTrcEB1).

(4) Expression of the bioB gene in *Escherichia coli*

*Escherichia coli* JM109 (pTrcEB1) was precultured at 37° C. overnight in LB medium containing 100 μg/ml ampicillin. 0.1 ml of the preculture was transferred to 5 ml of the same medium in a test tube. After cultivation at 37° C. for 3 hours, IPTG was added at 2 mM to induce the trc promoter, and cultivation was continued for 4 hours. Bacterial cells were collected and washed with saline. The cells were disrupted by sonication, and whole cell proteins were subjected to sodium dodecyl sulphate-polyacrylamide gel electrophoresis (SDS-PAGE) to confirm the expression of the bioB gene according to the protocol described by Laemmli [Nature, 227, 680–685 (1970)]. BIOB was overproduced in quantities of about 2% of whole cell proteins.

EXAMPLE 2

Isolation of BIOB

*Escherichia coli* JM109 (pTrcEB1) cells were aerobically cultivated with 2 L of Terrific broth (TB; 24 g Yeast extract/Difco, 12 g Tryptone/Difco, 4 g glycerol, 2.31 g KH2PO4, 12.54 g K2HPO4 in 1 liter) containing 100 µg/ml of ampicillin at 37 C for 3 hours. BioB protein expression was induced by further cultivation for 3 hours after addition of 1 mM IPTG. Cells were harvested by centrifugation at 8000×g for 20 min., washed with 20 mM Tris-HCl/pH 8.1 (hereafter referred to as TB) containing 0.1 M NaCl and 1 mM EDTA. washed with the same buffer without 1 mM EDTA and stored at –80 C until use.

All column operations were effected at room temperature and other operations at 4–10 C unless otherwise stated. The BIOB was chased as protein band on SDS-PAGE (37 kDa molecular weight) corresponding with red band on column chromatographies. Cells were thawed with about 60 ml of TB containing 5 mM 2-mercaptoethanol (hereafter referred to as 2-ME) and disrupted by French press in the presence of 0.25 mM phenylmethylsulfonyl fluoride, 10 µg/ml deoxyribonuclease 1 and 10 µg/ml ribonuclease A, and cell debris was removed by centrifugation at 15000×g for 30 min. The solution was filled up to 200 ml with TB containing 5 mM 2-ME, and the same volume (200 ml) of TB containing 20% ammonium sulfate (w/v) was added to the solution. After addition of 1 mM EDTA, proteins in the solution were loaded on Phenyl-Toyopearl 650M (4.4×10 cm; Tosoh, Tokyo, Japan) which had been equilibrated with TB containing 2 mM 2–ME and 10% ammonium sulfate, washed with the same buffer and eluted with the same buffer without 10% ammonium sulfate. The eluted fraction was diluted 4-fold with TB containing 2 mM 2–ME and loaded on Q-Sepharose (4.4×10 cm, Pharmacia) which had been equilibrated with TB containing 2 mM 2-ME. After washing with the same buffer, elution was effected with 1200 ml of 0–0.5M NaCl linear gradient. The BIOB peak around 0.3 M NaCl concentration was collected, ammonium sulfate was added to 10% (w/v) and the solution was loaded on Phenyl-Toyopearl 650S (2.2×5 cm, Tosoh) which had been equilibrated with TB containing 2 mM 2-ME and 10% ammonium sulfate (w/v). After washing with the same buffer, elution was effected with 250 ml of 10–0% ammonium sulfate (w/v) linear gradient. The BIOB peak around 6% artmmonium sulfate concentration was collected, concentrated to about 3 ml by Centriprep-30 (Amicon) and passed through HiPrep Sephacryl S200HR 26/60 (Pharmacia) with TB containing 2 mM 2-ME and 0.25 M NaCl. The BIOB peak with red color was collected, diluted with the same volume of TB containing 2 mM 2-ME and loaded on RESOURCE Q 6 ml (Pharmacia) which had been equilibrated with the same buffer. After washing, elution was effected with 120 ml of 0–0.5 M NaCl linear gradient. The BIOB peak with red color was collected. Before storage, the BIOB was once diluted to a final protein concentration of about 1 mg/ml with 50 mM Tris-HCl/pH 8.1 containing 1 mM dithiothreitol (hereafter referred to as DTT) and anaerobically incubated with 100 µM $FeCl_3$ and 50 µM Na2S at room temperature for 2 hours. Excess ions and DTT were removed by passing through Sephadex G-25 (M, 1.5×18 cm, Pharmacia) with 0.1M Tris-HCl/pH 7.5 containing 0.2 mM DTT. The BioB Protein was concentrated to a final protein concentration of 20–30 mg/ml and stored at –80° C. Purity of the BioB protein prepared as above was estimated to be over 80% by a single protein band with about 37 kDa molecular weight on SDS-PAGE. The BioB protein prepared as above showed a typical absorption spectrum pattern of iron-sulfur proteins.

EXAMPLE 3

Cloning and Expression of Klebsiella nifU and nifS genes (1) Preparation of the Whole DNA

*Klebsiella pnetinoniae* strain M5a1 [Nature, 237, 102 (1972)] was grown in 50 ml of LB medium at 37° C. for 10 hours, and bacterial cells were recovered by centrifugation. The whole DNA was extracted from cells by the phenol method.

(2) Preparation of the Genomic Library

The cloning of *Klebsiella pneinioniae* nifU and nifS genes was performed. The whole DNA (2 µg) was completely digested with BamHI, and 2.3–2.6 kb of DNA fragments were obtained by the agarose gel electrophoresis. The vector plasmid pUC19 (Takara Shuzo Co.) was completely digested with BamHI, and then treated with alkaline phosphatase to avoid self-ligation. The genomic DNA fragments prepared above were ligated with the cleaved pUC19 using the DNA ligation Kit (Takara Shuzo Co.), and the ligation mixture was transferred into *Escherichia coli* strain JM109 by a suitable cell method. The strains were selected for ampicillin resistance (100µg/ml) on LB medium agar plate. 2,000 of individual clones having the genomic DNA fragments were obtained as a genomic library.

(3) Selection of the clone having *Klebsiella pneinioniae* nifU and nifS genes

The selection of the clone having *Klebsiella pneinioniae* nifU and nifS genes was carried out by colony hybridization according to the protocol described by Maniatis et al. (Molecular Cloning, Cold Spring Harbor Laboratory Press 1982, pp. 326–328).

The grown colonies on the agar plate were transferred to nylon membranes (Hybond-N, Amersham Co.) and lysed by alkali. The denatured DNA was then inmmobilized on the membranes. Hybridization was performed using the DIG DNA Labeling and Detection system (Boehringer Mannheim Co., Mannheim, Germany ) according to the instructions of manufacturer. Two oligonucleotides having partial sequences of the nifU and nifS genes were synthesized. The sequences are shown as follows:

nifU-probe SEQ ID NO:1 5' AGAGGAGCACGAC-GAGGGCAAGCTGATCTGCAAAT nifS-probe SEQ ID NO:2 5' CGTTGGTCAGCGTGAT-GTGGGCGAATAACGAAACC 3'-Ends of the oligonucleotides were labeled using the DIG Oligonucleotide 3'-End Labeling Kit (Boehringer Mannheim Co.), and a mixture of the labeled oligonucleotide was used as a probe for hybridization. Hybridized clones were detected using the DIG Luminescent Detection Kit (Boeltringer Mannheim Co.). Twenty-six candidates for the clone bearing the nifU and nifS genes were obtained.

Four candidates were chosen, and the transformants having the candidates were grown in LB medium containing 100 µg/ml ampicillin. The hybrid plasmids were extracted from the cells by the alkaline-denaturation method and analyzed using restriction enzymes (BamHI, VspI and ScaI). 300–400 of nucleotide sequences from both ends of inserted DNA fragments were determined using the ALFred DNA sequencer (Pharmnacia Biotech Co.). The determined sequences were identical to the nucleotide sequence of *Klebsiella pneumoniae* nifU, S cluster published by Beynon [J. Bacteriol. 169, 4024–4029 (1987)]. These results showed that the obtained clones had *Klebsiella pneumoniae* nifU, S cluster. The hybrid plasmid in which the nifU, S cluster was inserted in the same direction as the lactose (lac) promoter in the vector was named pKNnif01. The hybrid plasmid having the nifU, S cluster inserted in opposite direction to the lac promoter was named pKNnif02.

(4) Construction of Hybrid Plasmid pKNnif03

The vector plasmid pBluescriptII-SK$^+$ (Toyobo Co., Tokyo, Japan) was completely digested with HincII and BamHI. The hybrid plasmid pKlnif02 was completely digested with VspI. The cleaved pKNnif02 was blunted with the DNA Blunting Kit (Takara Shuzo Co., Japan) and completely digested with BamHI. A 2.4 kb of fragment containing the nifU, S cluster was obtained by the agarose gel electrophoresis. The 2.4 kb of fragment was inserted to the cleaved pBluescriptII-SK$^+$ using the DNA ligation Kit to obtain the hybrid plasmid pKNnif03.

(5) Construction of the Hybrid Plasmid pKNnif04

The vector plasmid pTrc99A was completely digested with KpnI and BamHI. The hvbrid plasmid pKnif03 was completely digested with KpnI and BamHI, and a 2.4 kb of KpnI-BamHI fragment containing the nifU, S cluster was obtained by the agarose gel electrophoresis. The 2.4 kb of fragment was ligated with the cleaved pTrc99A using the DNA ligation Kit. The hybrid plasmid pKNnif04 in which the nifU, S cluster was inserted at the downstream of the trc promoter was finally obtained. *Escherichia coli* strain JM109 having this hybrid plasmid was named *Escherichia coli* JM109 (pKNnif04).

(6) Expression of the Klebsiella nifU and nifS genes

Escherichia coli JM109 (pKNnif04) was precultured at 30° C. overnight in LB medium containing 100 μg/ml ampicillin. 0.1 ml of the preculture was transferred to 5 ml of the same medium in a test tube. After cultivation at 30° C. for 3 hour, IPTG was added at 1 mM to induce the trc promoter, and cultivation was continued for 3 hours. Bacterial cells were collected and washed with saline. The cells were disrupted by sonication, and whole cell proteins were subjected to SDS-PAGE to confirm the expressions of the nifU and nifS genes according to the protocol described by Laemmli [Nature, 227, 680–685 (1970)]. NIFU and NIFS were overproduced in the cells.

EXAMPLE 4

Preparation of the cell-free extract of *Escherichia coli* with/without NIFU and NIFS

*Escherichia coli* JM109 (pKNnif04) and *Escherichia coli* JM109 (pTrc99A) cells were aerobically cultivated with Terrific broth (see Example 2) containing 100 μg/ml of ampicillin at 30 C for 3 hours. nifU and NIFS expression was induced by further cultivation for 3 hours after addition of 1 mM IPTG. Cells were harvested by centrifugation at 8000×g for 20 min., washed once with TB containing 0.1 M NaCl and 1 mM EDTA, washed twice with the same buffer without 1 mM EDTA and stored at −80 C until use.

Cell-free extract of each strain was prepared as follows. Cells were thawed and suspended in about 2 volumes of 0.1 M Tris-HCl/pH 7.5 containing 0.2 mM 2-ME against wet cell weight. Cells in the suspension were degassed, purged by argon gas and disrupted by sonicator (Bioruptor, Cosmo Bio) in a sealed tube with argon. Insoluble materials were removed by centrifugation at 100000×g for 30 min. The resulting supernatant was used as the cell-free extract. Total protein concentration of the cell-free extracts was determined by BCA protein assay system (PIERCE, Rockford, Ill. 61105, USA) after protein precipitation by 6% trichloroacetic acid and protein washing with acetone. Cell-free extracts with about 30 mg/ml protein concentration were obtained by the above method. Cell-free extracts of *Escherichia coli* JM109 (pKNnif04) expressing NIFU and NIFS showed remarkable red color comparing with that of *Escherichia coli* JM109 harboring pTrc99A at the same protein concentration. as Cell-tree extracts were stored at −80 C with argon in sealed tubes.

EXAMPLE 5

In vitro enzyme reaction (DAF system)

The enzyme reaction mixture contained 100 μM desthiobiotin, 1000 μM S-adenosyl-methionine [SAM], 200 μM L-cysteine, 50 μM deazariboflavin [DAF], 0.6 mg/ml (16 μM) BIOB protein, 20 mg protein/ml of the mixture of the cell-free extracts from *Escherichia coli* JM109 (pKNnif04) and *Escherichia coli* JM109 (pTrc99A), and 0.1 M Tris-HCl/pH 7.5 in a total volume of 50 μl. The enzyme reaction mixture in a 300 μl glass tapered ended tube was brought to anaerobic condition by repetition of weak aspiration and argon pressure under darkness. The reaction was started at 30° C. by light irradiation with a 20 W fluorescent bulb located 10 cm away. After 80 min. reaction, the reaction was stopped by heating at 95 C, and the produced biotin was determined by the microbiological assay using *Lactobccillus plintarim* (ATCC8014). Two kinds of cell-free extracts derived from *Escherichia coli* JM109 (pKNnif04) and *Escherichia coli* JM109 (pTrc99A) were mixed at various ratios at the constant protein concentration of 20 mg/ml in the reaction mixtures. In accordance with the increase of the ratio of the cell-free extract from *Escherichia coli* JM109 (pKNnif04) which expressed NIFU and NIFS proteins, a significant increase of biotin production was observed. About 1.8-fold higher biotin production than the control was observed when the content of the cell-free extract from *Escherichia coli* JM109 (pKNnif04) was 64% (see Table 1).

TABLE 1

| Ratio of B:A (%) | Produced biotin (ng/ml) | Relative index (%) |
| --- | --- | --- |
| 0:100 (Control) | 532.8 | 100 |
| 16:84 | 688.3 | 129.2 |
| 32:68 | 829.8 | 155.7 |
| 64:36 | 927.3 | 174.0 |
| 100:0 | 811.3 | 152.3 |

Remarks:
A = cell-free extract from *Escherichia coli* JM109(pTrc99A)
B = cell-free extract from *Escherichia coli* JM 109(pKNnif04)

EXAMPLE 6

Construction of *Escherichia coli* strain co-expressing the bioB, nifU and nifS genes (1) Construction of the hybrid plasmid pKNnif05

The vector plasmid pMW218 (Nippon Gene Co., Tokyo, Japan) was completely digested with KpnI and BamHI. The 2.4 kb of KpnI- BamHI fragment carrying the nifU, S cluster obtained from the hybrid plasmid pKNnif03 in Example 3 was ligated with the cleaved pMW218 using the DNA ligation Kit. The hybrid plasmid pKNnif05 in which the nifU, S cluster was inserted at the downstream of the lac promoter was finally obtained.

The vector plasmid pMW218 and the hybrid plasmid pKNnif05 were transferred to *Escherichia coli* JM109 (pTrcEB1) by a suitable cell method, and transformants were selected on LB medium agar plate containing 100 μg/ml ampicillin and 10 μg/ml kanamycin.

*Escherichia coli* strain JM109 having the hybrid plasmid pTrcEB1 and the vector plasmid pMW218 was named *Escherichia coli* JM09 (pTrcEB1 and pMW218). *Escherichia coli* strain JM109 having the hybrid plasmids pTrcEB1 and pKiNnif05 was named *Escherichia coli* JM109 (pTrcEB1. pKNnif05).

(2) Construction of the hybrid plasmid pKNnif06

The hybrid plasmid pTrcEB1 was completely digested with BamHI and treated with alkaline phosphatase to avoid self ligation. The hybrid plasmid pKNnif02 was completely digested with VspI. The cleaved pKNnif02 was blunted with the DNA Blunting Kit and ligated with BamHI linker (Takara Shuzo Co.) using the DNA ligation Kit. After complete digestion with BamHI, a 2.4 kb of BamHI fragment containing the nifU, S cluster was obtained by the agarose gel electrophoresis. The 2.4 kb of fragment was inserted to the cleaved pTrcEB1 using the DNA ligation Kit. The hybrid plasmid pKNnif06 in which the bioB, nifU and nifS genes were inserted at the downstream of the trc promoter was finally obtained. *Escherichia coli* strain JM109 having this hybrid plasmid was named *Escherichia coli* JM109 (pKNnif06).

(3) Co-expression of the bioB, nifU and nifS genes in *Escherichia coli*

*Escherichia coli* JM109 (pTrcEB1, pKNnif05) and *Escherichia coli* JM109 (pKiNnif06) were precultured at 30° C. overnight in LB medium containing 100 μg/ml ampicillin and 10 μg/ml kanamycin and in LB medium containing 100 μg/ml ampicillin, respectively. 0.1 ml of the precultures were transferred to 5 ml of the same medium in test tubes. After cultivation at 30° C. for 3 hours, IPTG was added at 1 mM for the induction, and cultivation was continued for 3 hours. Bacterial cells were collected and washed with saline. The cells were disrupted by sonication, and whole cell proteins were subjected to SDS-PAGE to confirm the expressions of the bioB, nifU and nifS genes according to the protocol described by Laemmli [Nature, 227, 680–685 (1970)]. BIOB, NIFU and NIFS proteins were found to be overproduced together in the cells.

EXAMPLE 7

Biotin production by fermentation (1) Biotin production by *Escherichia coli* JM109 (pTrcEB1, pKNnif05) and *Escherichia coli* JM109 (pKNnitf06)

*Escherichia coli* JM109 (pTrcEB1, pMW218) and *Escherichia coli* JM109 (pTrcEB1, pKNnif05) were inoculated into 50 ml of PC medium (2% glycerol, 5% protease peptone, 2% casamino acid, 1% K2HPO4, 0.05% KCl, 0.05% MgSO4 7H2O, 0.001% MnSO4 4-6H2O, 0.001% FeSO4 7H2O; pH7.0) containing 100 μg/ml ampicillin, 10 μg/ml kanamycin and 200 μg/ml desthiobiotin, and subjected to shaking culture at 30° C. for 3 hours. Then, IPTG was added at 1 mM to induce the trc promoter, and shaking culture was carried out at 30° C. for 27 hours. *Escherichia coli* JM109 (pTrc99A), *Escherichia coli* JM109 (pTrcEB1) and *Escheerichia coli* JM109 (pKNnif06) were inoculated into 50 ml of PC medium containing 100 μg/ml ampicillin and 200 μg/ml desthiobiotin, and cultivated in the same way as described above.

After the cultivation, 1.5 ml of the culture broth was centrifuged to remove bacterial cells. and the supernatant was obtained. Biotin production in the supernatant was assayed by the microbiological assay using *Lactobacillits plantarum* (ATCC8014). The average of the amounts of biotin produced by the four strains is shown in Table 2.

TABLE 2

| Strain Number | Biotin (mg/L) |
|---|---|
| JM109 (pTrc99A) | 0 |
| JM109 (pTrcEB1) | 2.03 |
| JM109 (pTrcEB1, pMW218) | 2.61 |
| JM109 (pTrcEB1, pKNnif05) | 4.00 |
| JM109 (pKNnif06) | 4.71 |

EXAMPLE 8

Isolation of NIFU and NIFS

*Escherichia coli* JM109 (pKTnif04) cells were aerobically cultivated with 1 L of Terrific broth containing 100 μg/ml of ampicillin at 26° C. for 3 hours. The NIFU and NIFS gene expression was induced by further cultivation for 3 hours after addition of 1 mM IPTG. Cells (5.4 g wet weight) were harvested by centrifugation at 8,000×g for 20 min, washed with 20 mM Tris-HCl/pH 7.4 containing 0.1 M NaCl and 1 mM EDTA, washed with the same buffer without 1 mM EDTA twice and stocked at −80° C. until use.

All column operations were anaerobically performed at room temperature and other operations were anaerobically performed at 4–10C unless otherwise stated. The NIFU and NIFS proteins were chased as protein bands on SDS-PAGE. The cells were thawed with about 40 ml of 20 mM Tris-HCl/pH 7.4 containing 5 mM dithiothreitol (hereafter referred to DTT) and disrupted by French press in the presence of 0.5 mM phenylmethylsulfonyl fluoride, 10 μg/ml deoxyribonuclease I, 10 μg/ml ribonuclease A and 5 mM pyridoxal phosphate. The cell debris was removed by centrifugation at 7,700×g for 30 min and the insoluble fraction was removed by centrifugation at 48,000×g for 30 min. The solution was filled up to 50 ml with the same buffer and streptomycin sulfate was added to the solution at final concentration of 1% (w/v). The insoluble residue was removed by centrifugation at 48,000×g for 20 min and solid ammonium sulfate was added to the supernatant to 30% saturation. After gently stirring at room temperature for 10 min, the precipitate containing NIFU and NIFS proteins was obtained by centrifugation at 48,000×g for 10 min. The precipitate was resuspended in 20 mM Tris-HCl/pH 7.4 containing 5 mM DTT, and the supernatant obtained by centrifugation at 48,000×g for 30 min was loaded on RESOURCE Q (6 ml, Pharmacia) which had been equilibrated with 20 mM Tris-HCl/pH 7.4 containing 5 mM DTT. After washing with the same buffer, elution was done by 150 ml of 0–0.5 M NaCl linear gradient. The NIFU and NIFS proteins were co-eluted in 20 ml of fraction around 0.3 M NaCl, and the fraction was collected and concentrated to 3.5 ml by PM-30 (Amicon). The concentrated protein solution was passed through HiPrep Sephacryl S-200 HR 26/60 (Pharmacia) with 20 mM Tris-HCl/pH 7.4 containing 5 mM DTT and 0.25 M NaCl. All NIFS protein was recovered as a protein complex with NIFU protein, and some part of NIFU protein as a monomer. The NIFU/S complex was eluted at about 140 kDa molecular weight position. and the NIFU monomer was eluted at about 35 kDa molecular weight position. The 18 ml of fraction containing the NIFU/S complex and the 24 ml of fraction containing the NIFU monomer were concentrated to 3 ml by CentriPlus-30 (Amicon) and stocked at −80° C.

EXAMPLE 9

Effects of the purified NIFU/S complex and NIFU monomer on biotin formation

The enzyme reaction mixture without cell-free extracts contained 100 μM desthiobiotin. 1000 μM SAM, 200 μM L-cysteine, 50 μM deazariboflavin, 0.6 mg/ml (16 μM) BIOB protein, 10 mM DTT and 0.1 M Tris-HCl/pH 7.5 in total volume of 50 μl. The enzyme reaction mixture in a 300 μl glass spitz tube was brought to anaerobic condition by repeating of weak aspiration and argon pressure under dark. The reaction was started by light irradiation from 10 cm distance with 20 W fluorescent bulb at 30° C. After 80 min reaction, reaction was stopped by heating at 95° C., and produced biotin was determined by the microbiological assay 1 ) using *Lactobacillis plantarum*. (ATCC8014)

Effect of additions of the purified NIFU/S complex and/or the purified NIFU monomer on the enzyme reaction mixture was examined. Addition of 13 μM the purified NIFU/S complex or 30 μM NIFU monomer showed about 4-fold higher biotin production. Addition of both 13 μM the purified NIFU/S complex and 30 μM NIFU monomer showed about 9-fold higher biotin production. (see Table 3)

TABLE 3

| 13 μM NIFU/S complex | 30 μM NIFU monomer | Produced biotin (ng/ml) |
|---|---|---|
| − | − | 54.15 |
| + | − | 202.75 |
| − | + | 203.51 |
| + | + | 453.83 |

What is claimed is:
1. A process for making biotin comprising the steps of:
   (a) contacting desthiobiotin with an enzyme reaction mixture comprising:
      (i) a bioB gene product,
      (ii) an additional gene product selected from the group consisting of a nifU gene product, a nifS gene product, and a combination thereof, and
      (iii) an effective amount to form biotin of:
         (1) S-adenosylmethionine,
         (2) L-cysteine, and
         (3) a first electron donor system comprising ferredoxin-NADP reductase, flavodoxin, and NADPH or a second electron donor system selected from the group consisting of deazariboflavin, deazaflavin, and 8-hydroxy-5-deazaflavin, wherein the second electron donor system is reduced; and
   (b) isolating biotin from the reaction mixture.
2. The process of claim 1, wherein the additional gene product is nifU.
3. The process of claim 1, wherein the additional gene product is nifS.
4. The process of claim 1, wherein the additional gene product is a combination of nifS and nifU.
5. The process of claim 1, wherein the bioB gene product is obtained from *Escherichia coli*.
6. The process of claim 1, wherein the nifU gene product is obtained from *Klebsiella pneumoniae*.
7. The process of claim 1, wherein the nifS nifU gene product is obtained from *Klebsiella pneumoniae*.
8. The process of claim 1, wherein the enzyme reaction mixture is cell-free.
9. A process for making biotin comprising the steps of:
   (a) contacting desthiobiotin with an enzyme reaction mixture comprising:
      (i) a bioB gene product,
      (ii) a nifU gene product,
      (iii) a nifS gene product,
      (iv) an effective amount to form biotin of:

---

SEQUENCE LISTING

<160> NUMBER OF SEQ ID NOS: 2

<210> SEQ ID NO 1
<211> LENGTH: 35
<212> TYPE: DNA
<213> ORGANISM: Unknown Organism
<220> FEATURE:
<223> OTHER INFORMATION: Description of Unknown Organism: unknown

<400> SEQUENCE: 1
agaggagcac gacgagggca agctgatctg caaat            35

<210> SEQ ID NO 2
<211> LENGTH: 35
<212> TYPE: DNA
<213> ORGANISM: Unknown Organism
<220> FEATURE:
<223> OTHER INFORMATION: Description of Unknown Organism: Unknown

<400> SEQUENCE: 2
cgttggtcag cgtgatgtgg gcgaataacg aaacc            35

(1) S-adenosylmethionine,
(2) L-cysteine, and
(3) a first electron donor system comprising ferredoxin-NADP reductase, flavodoxin, and NADPH or a second electron donor system selected from the group consisting of deazariboflavin, deazaflavin, and 8-hydroxy-5-deazaflavin, wherein the second electron donor system is reduced; and (b) isolating biotin from the reaction mixture.

10. The process of claim 9, wherein the bioB gene product is obtained from *Escherichia coli*.

11. The process of claim 9, wherein the nifU gene product is obtained from *Klebsiella pneumoniae*.

12. The process of claim 9, wherein the nifS nifU gene product is obtained from *Kiebsiella pneumoniae*.

13. The process of claim 9, wherein the enzyme reaction mixture is cell-free.

\* \* \* \* \*

UNITED STATES PATENT AND TRADEMARK OFFICE
CERTIFICATE OF CORRECTION

PATENT NO. : 6,361,978 B1
DATED : March 26, 2002
INVENTOR(S) : Tatsuo Hoshino et al.

It is certified that error appears in the above-identified patent and that said Letters Patent is hereby corrected as shown below:

<u>Title page,</u>
Item [73], Assignee, please change "Parsipanny" to -- Parsippany --;

<u>Column 16,</u>
Lines 5 and 7, please italicize "bioB," "nifU," and "nifS";
Line 20, please italicize "nifU";
Line 22, please italicize "nifS";
Line 24, please italicize "nifU," and "nifS";
Line 24, please italicize "bioB";
Line 26, please italicize "nifU";
Line 28, please italicize "nifU," and "nifS";
Lines 35-37, please italicize "bioB," "nifU," and "nifS";

<u>Column 18,</u>
Line 1, please italicize "bioB";
Line 3, please italicize "nifU";
Line 5, please italicize "nifS";
Line 5, please delete "nifU";
Line 6, please change "Kiebsiella" to -- Klebsiella --.

Signed and Sealed this

Fifth Day of August, 2003

JAMES E. ROGAN
*Director of the United States Patent and Trademark Office*